(12) United States Patent

Haghighi-Mood et al.

(10) Patent No.: US 12,599,431 B2

(45) Date of Patent: Apr. 14, 2026

(54) CATHETER AND METHOD FOR IMPROVED IRRIGATION

(71) Applicant: Sirona Medical Technologies, Inc., Andover, MA (US)

(72) Inventors: Ali Haghighi-Mood, Andover, MA (US); Richard Jonathan Cohen, Newton, MA (US)

(73) Assignee: Sirona Medical Technologies, Inc., Andover, MA (US)

( * ) Notice: Subject to any disclaimer, the term of this patent is extended or adjusted under 35 U.S.C. 154(b) by 997 days.

(21) Appl. No.: 17/229,405

(22) Filed: Apr. 13, 2021

(65) Prior Publication Data

US 2021/0228271 A1     Jul. 29, 2021

Related U.S. Application Data

(60) Continuation of application No. 16/659,923, filed on Oct. 22, 2019, now Pat. No. 11,103,306, which is a (Continued)

(51) Int. Cl.
    *A61B 18/14*     (2006.01)
    *A61B 18/00*     (2006.01)

(52) U.S. Cl.
    CPC ..................... *A61B 18/1492* (2013.01); *A61B 2018/00029* (2013.01); *A61B 2018/0022* (2013.01);

(Continued)

(58) Field of Classification Search
    CPC ...... A61B 18/1492; A61B 2018/00577; A61B 2018/00744; A61B 2218/002
    See application file for complete search history.

(56) References Cited

U.S. PATENT DOCUMENTS

| | | | |
|---|---|---|---|
| 4,940,064 A | 7/1990 | Desai | |
| 5,230,349 A | 7/1993 | Langberg | |

(Continued)

FOREIGN PATENT DOCUMENTS

| | | | |
|---|---|---|---|
| CN | 1674836 A | 9/2005 | |
| EP | 1245196 A1 | 10/2002 | |

(Continued)

OTHER PUBLICATIONS

Demazumder et al. (Dec. 2001) "Comparison of Irrigated Electrode Designs for Radiofrequency Ablation of Myocardium", Journal of Interventional Cardiac Electrophysiology, 5(4):391-400.

(Continued)

*Primary Examiner* — Linda C Dvorak
*Assistant Examiner* — Christine A Dedoulis
(74) *Attorney, Agent, or Firm* — Mintz, Levin, Cohn, Ferris, Glovsky and Popeo, P.C.

(57) ABSTRACT

Various catheters with expandable and contractible fluid pathways extending therethrough, and methods of use, are provided herein. In an exemplary embodiment, a catheter is provided with an elongate body having an electrode at the distal end thereof. One or more expandable members or wings can extend between the electrode and the distal end of the elongate body. The catheter can also include an actuator extending therethrough and coupled to the electrode such that movement of the actuator is effective to advance and retract the electrode, thereby moving the one or more expandable members between a collapsed configuration and an expanded configuration. The catheter can also include a fluid sealed lumen formed therein and configured to receive fluid and to deliver fluid to one or more pathways formed in the electrode. The actuator can extend through the fluid sealed lumen, however it can be fluidly separated from the lumen. The fluid sealed lumen can be configured to expand (Continued)

and collapse with movement of the electrode, while allowing movement of the actuator therethrough.

17 Claims, 7 Drawing Sheets

Related U.S. Application Data division of application No. 16/140,095, filed on Sep. 24, 2018, now Pat. No. 10,485,611.

(60) Provisional application No. 62/562,934, filed on Sep. 25, 2017.

(52) U.S. Cl.
CPC .............. *A61B 2018/00267* (2013.01); *A61B 2018/00351* (2013.01); *A61B 2018/00577* (2013.01); *A61B 2018/00744* (2013.01); *A61B 2018/00791* (2013.01); *A61B 2218/002* (2013.01)

(56) References Cited

U.S. PATENT DOCUMENTS

| | | | |
|---|---|---|---|
| 5,342,357 | A | 8/1994 | Nardella |
| 5,688,267 | A | 11/1997 | Panescu et al. |
| 5,897,553 | A | 4/1999 | Mulier et al. |
| 6,522,905 | B2 | 2/2003 | Desai |
| 6,635,047 | B2* | 10/2003 | Forsberg ........... A61M 25/0045 |
| | | | 604/525 |
| 6,738,673 | B2 | 5/2004 | Desai |
| 7,151,964 | B2 | 12/2006 | Desai et al. |
| 7,632,266 | B2 | 12/2009 | Scopton et al. |
| 7,857,810 | B2* | 12/2010 | Wang ................... A61B 18/148 |
| | | | 606/41 |
| 8,882,761 | B2 | 11/2014 | Desai |
| 9,192,308 | B2* | 11/2015 | Brannan .................. A61B 5/01 |
| 9,717,558 | B2 | 8/2017 | Desai |
| 9,943,363 | B2 | 4/2018 | Clark et al. |
| 10,485,611 | B2 | 11/2019 | Haghighi-Mood et al. |

| | | | |
|---|---|---|---|
| 2002/0062123 | A1 | 5/2002 | Mcclurken et al. |
| 2004/0243119 | A1 | 12/2004 | Lane et al. |
| 2005/0070894 | A1 | 3/2005 | Mcclurken |
| 2005/0090816 | A1 | 4/2005 | Mcclurken et al. |
| 2006/0079873 | A1 | 4/2006 | Scopton et al. |
| 2006/0184165 | A1 | 8/2006 | Webster et al. |
| 2008/0045943 | A1 | 2/2008 | Wittkampf et al. |
| 2008/0161792 | A1 | 7/2008 | Wang et al. |
| 2008/0275440 | A1 | 11/2008 | Kratoska et al. |
| 2010/0016848 | A1 | 1/2010 | Desai |
| 2010/0053015 | A1 | 3/2010 | Willyard |
| 2013/0131145 | A1 | 5/2013 | Carthew et al. |
| 2015/0066017 | A1 | 3/2015 | Desai |
| 2015/0073409 | A1 | 3/2015 | Watson et al. |
| 2016/0175009 | A1 | 6/2016 | Davies et al. |
| 2016/0206371 | A1 | 7/2016 | Elgaard et al. |
| 2017/0143201 | A1 | 5/2017 | Claude et al. |
| 2017/0319274 | A1* | 11/2017 | Desai ................. A61B 18/1492 |
| 2018/0140807 | A1 | 5/2018 | Herrera et al. |
| 2019/0090942 | A1 | 3/2019 | Jaghighi-Mood et al. |
| 2020/0054393 | A1 | 2/2020 | Haghighi-Mood et al. |

FOREIGN PATENT DOCUMENTS

| | | |
|---|---|---|
| JP | H11504539 A | 4/1999 |
| JP | H11506947 A | 6/1999 |
| JP | 2000201949 A | 7/2000 |
| JP | 2005502424 | 1/2005 |
| WO | 9618349 A2 | 6/1996 |
| WO | 03020339 A2 | 3/2003 |
| WO | 03024349 A1 | 3/2003 |
| WO | 2019060833 A1 | 3/2019 |

OTHER PUBLICATIONS

Nakagawa et al. (1998) "Inverse Relationship Between Electrode Size and Lesion Size During Radiofrequency Ablation With Active Electrode Cooling", Circulation, 98(5):458-465.

Wittkampf et al. (Nov. 2006) "RF Catheter Ablation: Lessons on Lesions", Pacing and Clinical Electrophysiology, 29(11):1285-1297.

* cited by examiner

CATHETER AND METHOD FOR IMPROVED IRRIGATION

CROSS-REFERENCE TO RELATED APPLICATIONS

This application is a continuation of U.S. patent application Ser. No. 16/659,923, filed Oct. 22, 2019, entitled "Catheter and Method for Improved irrigation," which is a divisional application of U.S. patent application Ser. No. 16/140,095 (now U.S. Pat. No. 10,485,611), fled Sep. 24, 2018, entitled "Catheter and Method for Improved Irrigation," which claims priority to U.S. Provisional App. No. 62/562,934, filed Sep. 25, 2017, which are hereby incorporated by reference herein in their entireties.

FIELD

Catheters, and in particular irrigated ablation catheters, are provided, as well as methods for using the same.

BACKGROUND

A variety of operations require the use of a catheter to deliver irrigation to a surgical site. For example, treatment of cardiac arrhythmias often require locating in the heart the sites of origin of the arrhythmia or sites of abnormal conduction, and ablating these sites through delivery of radiofrequency energy through an electrode located at or near the tip of a catheter. However, if the temperature of the electrode and/or temperature of the immediately surrounding tissue become excessively high during such a procedure, the patient may suffer adverse consequences. In particular there is a risk of charring of the tissue in contact with the electrode, creating steam pops in the tissue and coagulating the surrounding blood. These undesired effects may lead to excess damage to the tissue compromising its physical integrity which could be catastrophic for the patient and/or increasing the risk of the patient suffering a stroke as a result of coagulated blood or tissue fragments propagating through the blood stream to the patient's brain. It can be desirable to attempt to reduce the risk of such undesirable effects by cooling the electrode and the tissue immediately surrounding the electrode by delivering irrigation fluid through or around the electrode. The irrigation fluid may exit through the electrode into the region immediately surrounding the electrode. However, effectively delivering such irrigation to a remote tissue site within the human body can present challenges.

Accordingly, there remains a need for catheters having improved irrigation and ablation abilities.

SUMMARY

Catheters having improved irrigation and ablation abilities are provided herein, as well as methods for treating tissue.

In one aspect, a catheter is provided that includes an elongate body with an electrode assembly on a distal end thereof. An actuator extends through the elongate body and couples to the electrode assembly such that longitudinal movement of the actuator moves the electrode assembly between a collapsed configuration and an expanded configuration. The elongate body has a fluid pathway extending therethrough for directing fluid to the electrode assembly. At least a portion of the fluid pathway is coaxially disposed around at least a portion of the actuator and is fluidly sealed from the actuator.

There can be numerous variations of the catheter. For example, the catheter can include a flexible seal disposed within the elongate body and around a portion of the actuator extending through the elongate body. The flexible seal can define a fluid barrier between the actuator and the fluid pathway in the housing. In another example, the flexible seal can have a proximal end coupled to a proximal end of the elongate body and a distal end coupled to the electrode assembly. In some embodiments, the elongate body can include first and second tubes therein, and the first and second tubes can be slidably coupled to one another and defining the fluid pathway. A flexible sleeve can also be disposed around the first and second tubes such that a first end of the sleeve is sealed to the first tube and a second end of the sleeve is sealed to the second tube, and the flexible sleeve can expand and contract when the first and second tubes slide relative to one another.

In another example, the elongate body can include a tube that is configured to expand radially outward in a direction perpendicular to a longitudinal axis of the elongate body when the electrode assembly is moved from the collapsed configuration to the expanded configuration. In still another example, a proximal end of the tube can be attached to the elongate body and a distal end of the tube can be attached to the electrode assembly, and the distal end of the tube can be fluidly sealed circumferentially to the electrode assembly. In some examples, the tube can be configured to bias the electrode assembly to the collapsed configuration. In another example, the tube comprises a metal braid coated with a flexible sealing material.

In another aspect, a catheter is provided that includes an elongate body having a proximal end, a distal end, and a lumen extending between the proximal and distal ends. An end effector assembly is at least partially disposed within the distal end of the elongate body, and the end effector assembly includes an expandable housing having a fluid sealed lumen therein. The housing has an inlet configured to allow fluid flow into the fluid sealed lumen and has an electrode at a distal end thereof with at least one fluid pathway extending therethrough that is configured to allow fluid flow out of the fluid sealed lumen. At least one expandable member extends between the distal end of the elongate body and the electrode, and the electrode is configured to distally advance and proximally retract relative to the elongate body to thereby move the housing between a collapsed configuration when the electrode is distally advanced and an expanded configuration when the electrode is proximally retracted.

The catheter can have a number of variations. For example, the catheter can include an actuator extending through the lumen in the elongate body and through the expandable housing of the end effector assembly. The actuator can have a distal end coupled to the electrode, and the actuator can be configured to move proximally and distally relative to the elongate body to distally advance and proximally retract the electrode. In another example, the expandable housing can comprise first and second tubes that are slidably coupled to one another and define the fluid sealed lumen.

In still another embodiment, the expandable housing can comprise a tube that is configured to expand radially outward in a direction perpendicular to a longitudinal axis of the elongate body when the housing is in the expanded configuration, and the tube can define the fluid sealed lumen. In one example, a proximal end of the tube can be attached to the distal end of the elongate body and a distal end of the tube can be attached to the electrode. In another example, the tube can be configured to bias the expandable housing to the collapsed configuration. In still another example, the tube can be configured to block energy passage across an outer surface thereof. In some embodiments, a volume inside the tube can change by about 25 percent or less when the housing moves between the collapsed and the expanded configurations.

In another aspect, a method for treating tissue is provided that includes advancing a catheter of an ablation device through a body lumen to position a distal end of the catheter adjacent to tissue to be treated. The method also includes retracting an actuator extending through the catheter to proximally retract an electrode coupled to a distal end of the actuator, and the proximal movement of the electrode causes an expandable body to move from a collapsed configuration to an expanded configured. The method also includes manipulating the catheter to position the electrode and the expandable body in contact with the tissue to be treated. The method includes actuating the ablation device to deliver energy to the electrode and to deliver fluid through at least one fluid pathway extending through the electrode, and the fluid can flow through an expandable fluid channel at least partially defined by the expandable body.

The method can have numerous variations. For example, retracting the actuator can cause first and second tubes of the expandable fluid channel to slide relative to each other while maintaining the expandable fluid channel therethrough.

In another embodiment, the expandable body can includes a tube such that, when the expandable body moves from the collapsed configuration to the expanded configured, the tube expands radially outward in a direction perpendicular to a longitudinal axis of the catheter. In one example, the expandable body can cover a part of the electrode not in contact with the tissue during delivery of energy to the electrode. In still another example, the expandable body can block energy from crossing an outer surface of the expandable body during delivery of energy to the electrode. In one example, the method can include releasing the actuator such that the expandable body reverts from the expanded configuration to the collapsed configuration because the expandable body is biased to the collapsed configuration.

BRIEF DESCRIPTION OF THE DRAWINGS

The invention will be more fully understood from the following detailed description taken in conjunction with the accompanying drawings, in which.

DETAILED DESCRIPTION

Figure 1:
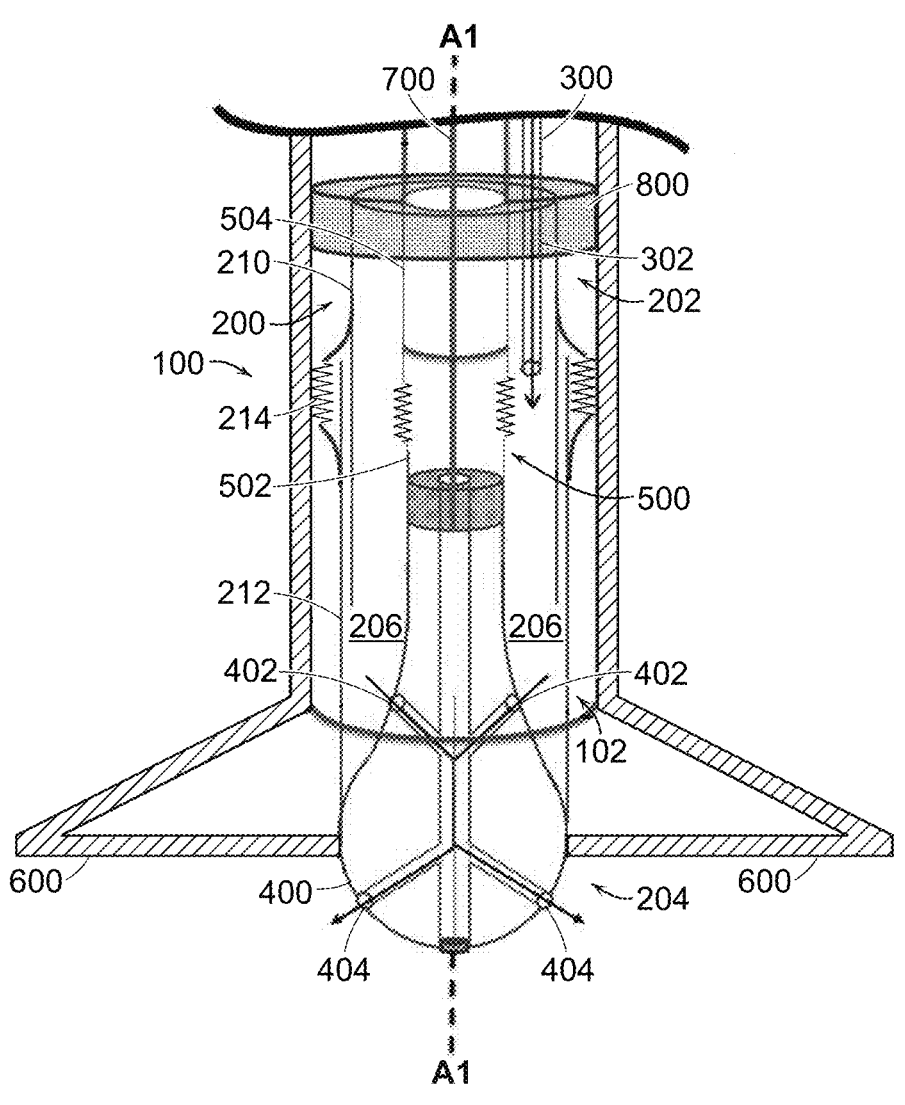
FIG. 1 is a cross-sectional, partially-perspective side view of one embodiment of a distal end of a catheter with an end effector in a deployed, expanded, vector state.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Many ablation catheters have an expandable end effector that is configured to move from a collapsed, linear configuration during delivery to a deployed, expanded configuration once positioned adjacent to a tissue to be treated. In order to deploy the end effector, an actuator extends through the body of the catheter and it connected to a portion of the end effector such that advancement and/or retraction of the actuator moves the end effector between the collapsed and expanded configurations. During ablation, energy is delivered to the tissue to form a lesion. While energy alone can be effective at forming a lesion, there is a risk of overheating the electrode and burning and/or charring the tissue. Accordingly, fluid can be delivered to the electrode to cool the electrode during energy delivery, thereby reducing the risk of causing undesirable damage to the tissue. However, effectively delivering irrigation fluid to the electrode can be difficult when the electrode used for delivery of the ablation energy or an electrode assembly at the tip of the catheter is movable with respect to a shaft of the catheter. For example, a central ablation electrode in a catheter disclosed in U.S. Pat. No. 8,882,761, filed Nov. 11, 2014 and incorporated herein in its entirety, is designed to be irrigated only when the catheter is in a deployed configuration but not in a linear non-deployed configuration or any time in between.

However, it can be desirable for the catheter to be able to be used for ablation of cardiac tissue when it is in the linear configuration, in the deployed configuration, or any configuration in between, and it can also be desirable to be able to adequately irrigate the ablation electrode(s) and immediately surrounding tissue in the linear non-deployed configuration, in the deployed configuration, or any configuration in between. This can be difficult to do so with many catheters because an irrigation fluid compartment within the catheter is often fixed with respect to a shaft of the catheter while the electrode assembly is movable with respect to the catheter shaft. Thus a catheter is provided herein in which an irrigation fluid pathway in the catheter is coupled to an electrode assembly which moves with respect to a shaft of the catheter. Since ablation catheters are required to have extremely small diameters, fluid delivery through a catheter having an actuator extending therethrough can be very challenging. More particularly, controlled and substantially constant flow of fluid to the electrode can be challenging. Constant fluid flow is especially desirable for uniform cooling of electrodes and/or tissue and thereby uniform delivery of RF power to the target site and creation of uniform lesions. Accordingly, various devices and methods are provided herein that allow fluid to be continuously delivered to an expandable end effector assembly at a substantially constant flow, while allowing an actuator to extend through the fluid pathway to couple to the end effector for deploying the end effector. Such fluid channels can also be incorporated into so called "basket" catheters, which involve a deployable basket incorporating a large number of electrodes to map electrically the entire inner surface of a cardiac chamber. It would be highly desirable to incorporate an ablation capability to such basket catheters, but again the irrigation of the electrodes used for delivering the ablation energy and the immediately surrounding tissue is difficult because of the need for coupling the irrigation fluid compartment in the catheter to the electrode assembly which moves with respect to the shaft of the catheter. Thus expandable and contractible fluid channels, as discussed herein, can be incorporated to provide effective ablation and irrigation to basket catheters.

A person skilled in the art will appreciate that, while ablation catheters are generally discussed herein, any catheter having an expandable end effector can be used in combination with the various fluid delivery techniques disclosed herein. In an exemplary embodiment, a catheter is provided with an elongate body that has a proximal end, a distal end, and a lumen extending therebetween. An end effector can be at least partially disposed within the distal end of the elongate body. The end effector can include an electrode at a distal end thereof with at least one fluid pathway extending therethrough. The end effector can also include an expandable and contractible fluid channel or pathway that is configured to receive and direct fluid to the at least one pathway in the electrode. Various structures are provided herein for defining the expandable and contractible fluid channel. The catheter can also include at least one expandable member or wing extending between the distal end of the elongate body and the electrode. In order to actuate the expandable member or wing, an actuator can extend through the elongate body and it can couple to the electrode. Longitudinal movement of the actuator can distally advance and proximally retract the electrode relative to the elongate body, which can cause the at least one expandable member or wing to move between an initial collapsed configuration and a deployed expanded configuration. In order to allow coupling between the actuator and the electrode, while still allow fluid delivery to the electrode, the actuator can extend through the structure defining the expandable and contractible fluid channel or pathway. The actuator can, however, be fluidly sealed from the expandable and contractible fluid channel or pathway to prevent fluid leakage. In use, movement of the actuator and electrode can cause expansion and contraction of the fluid channel or pathway, which can remain sealed. Because the structure defining the expandable and contractible fluid channel or pathway can expand and contract with movement of the electrode, the fluid channel or pathway can be maintained and fluid can be provided to the electrode at a substantially constant rate.

To achieve a substantially constant flow rate, it can be important to minimize or eliminate leaks. For example, couplings which leak may result in fluid moving out of a catheter compartment designed to contain the fluid into other elements of the catheter and/or into the tissue or blood surrounding the catheter. Fluid entering other elements of the catheter can impair or block functioning of those elements. Also, it can be helpful to closely control the amount of fluid delivered to cool one or more ablation electrodes and the surrounding tissue to make a lesion size predictable and the ablation procedure safe and effective. The fluid flow can be controlled by controlling pressure of the fluid reservoir external to the body and/or monitoring a fluid flow rate out of that reservoir. Thus when a leak is present, a relationship between the external pressure and externally measured fluid rate to the flow rate delivered to the desired locations to cool the electrode(s) and immediately surrounding tissue can no longer be reliably determined. For these reasons any leak in the irrigation system is undesirable.

Figure 2:
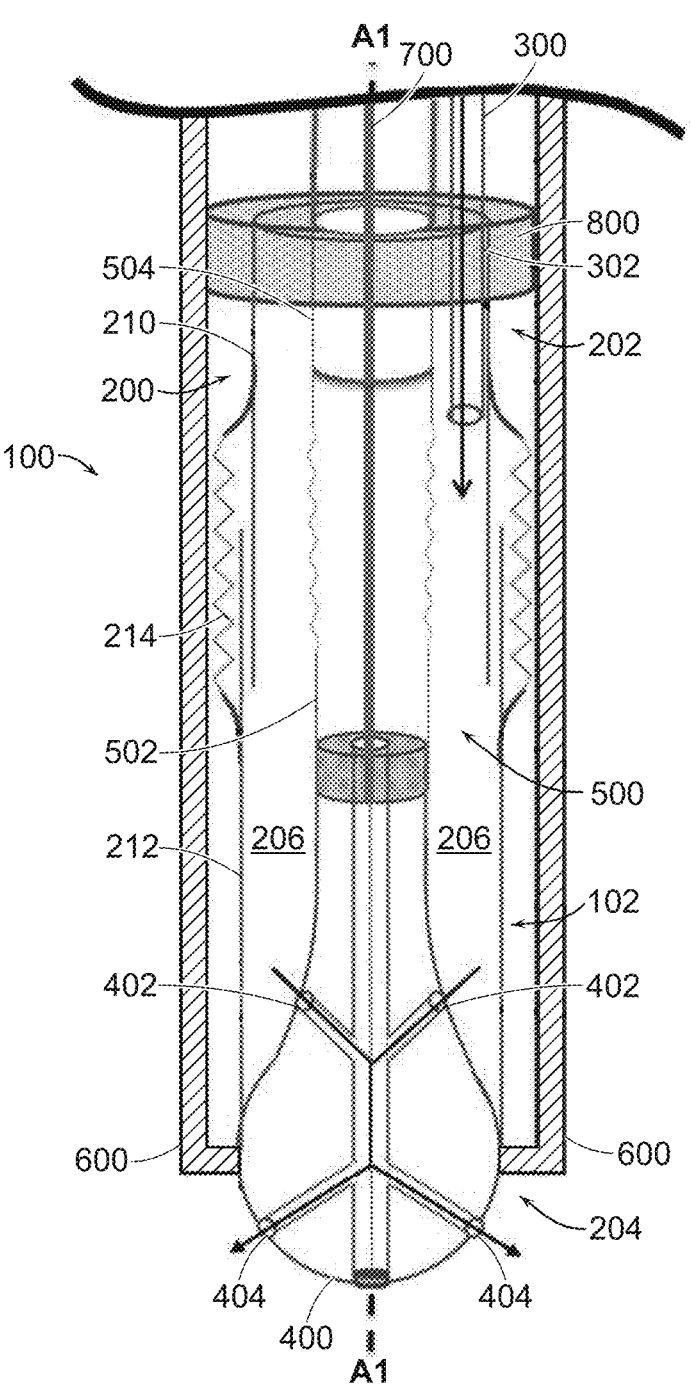
FIG. 2 is a cross-sectional side view of the distal end of the catheter of FIG. 1 with the end effector in a collapsed, linear state.

FIGS. 1 and 2 illustrate one embodiment of a distal end of a catheter with an elongate body 100. The elongate body 100 can be flexible and can have a proximal end, a distal end, and a lumen extending at least partially therethrough. An end effector 102 is disposed at least partially within the distal end of the elongate body 100. The end effector 102 can include an expandable and contractible housing 200 having a fluid inlet 302 at a proximal end and an electrode 400 at a distal end thereof and defining a fluid outlet in the form of at least one pathway formed therethrough. A fluid delivery tube 300 can extend through the elongate body 100 for delivering fluid to the housing 200. The catheter can also include at least one expandable member or wing 600 extending between the distal end of the elongate body 100 and the electrode 400, and an actuator 700 coupled to the electrode for actuating the end effector 102. In this embodiment, proximal movement of the actuator 700 can cause the electrode 400 to retract proximally, thereby causing the expandable member or wing(s) 600 to expand, as shown in FIG. 1, and distal movement of the actuator can cause distal advancement of the electrode body 100, which can cause the expandable member or wing(s) 600 to collapse or compress into a linear configuration, as shown in FIG. 2. For example, the catheter with the elongate body 100 can be maneuvered to a surgical site in the collapsed, linear configuration, as shown in FIG. 2. When at a treatment site, the catheter can either treat tissue in the linear configuration or it can be deployed into the expanded configuration, as shown in FIG. 1.

The end effector can have a variety of configurations, but as indicated above the end effector is preferably configured to allow advancement and retraction of the electrode using the actuator, while also allowing fluid to be delivered to the electrode. In the illustrated embodiment, the expandable and contractible housing 200 forms a proximal portion of the end effector with the electrode positioned at the distal end thereof. The expandable and contractible housing 200 can have a variety of configurations, but in an exemplary embodiment it is at least partially disposed in the elongate body 100 and at least a portion of it can be configured to move relative to and extend from the distal end of the elongate body 100. The housing 200 can be positioned co-axially with the elongate body 100 such that a longitudinal axis of the housing 200 corresponds to a longitudinal axis A1 of the elongate body 100. In order to define a fluid sealed lumen 206 extending therethrough, a distal end 204 of the housing 200 can be fixed to the electrode 400, and a proximal end 202 of the housing 200 can be sealed by and fixed within the elongate body 100. For example, a heat treatment can be applied to the elongate body to form a substantial end cap 800 on the housing 200, as will be discussed in more detail below. As indicated above, the housing 200 can be configured to expand and contract as the electrode 400 is pulled proximally and pushed distally during use. As illustrated in FIG. 1, the housing 200 can include an upper shaft or tube 210, a lower shaft or tube 212, and an expansion member 214. A proximal end of the expansion member 214 can be attached to the upper shaft 210, and a distal end of the expansion member 214 can be attached to the lower shaft 212. The upper shaft 210 can be fixed at its proximal end to the elongate body 100 and the lower shaft 212 can be fixed to the electrode 400, and one of the upper and lower shafts 210, 212 can be slidably disposed within the other one of the upper and lower shafts 210, 212. As a result, the lower shaft 212 can be configured to slidably move towards and away from the upper shaft 210 in coordination with to movement of the electrode 400. Such a configuration allows the housing 200 to expand and contract. As shown in FIG. 1, a distal end of the upper shaft 210 and a proximal end of the lower shaft 212 overlap one another when the housing 200 is in a deployed state. As shown in FIG. 2, the upper shaft 210 and the lower shaft 212 are moved away from each other in a linear state.

While the upper and lower shafts 210, 212 can be configured to sealing engage one another to prevent fluid leakage from the housing 200, in an exemplary embodiment the expansion member 214 forms a seal around the engagement portion between the two shafts 210, 212. The expansion member 214 can be configured to expand between the two shafts 210, 212 as the shafts 210, 212 slidably move away from each other, and to compress as the shafts 210, 212 move toward one another. The expansion member 214 will thus allow movement of the shafts 210, 212 while maintaining a seal in the fluid sealed lumen 206 within the housing 200 when the housing is in the expanded state or the contracted state. In certain aspects, a length of each of the shafts 210, 212 can be minimized because the expansion member 214 can prevent disengagement between the shafts 210, 212 in the expanded state while still providing a fluid sealed lumen 206 in the housing 200. Because lengths of the shafts 210, 212 can be minimized, an overall length of the housing 200 can be minimized, which allows for a smaller overall end effector length and thus more flexibility of the catheter.

The shafts 210, 212 can be made of stiffer materials relative to the expansion member 214, such as plastics, elastomers, metals, etc., and the expansion member 214 can be made of stretchable and compressible material, such as balloon-like materials, elastomers, plastics, etc. The expansion member 214 can have a variety of forms. For example, the expansion member 214 can be a stretchable, elastic tube. In some situations, a volume of an elastic tube can change when it is stretched, which can result in blood being sucked into the catheter when the catheter configuration is moved between a deployed state and a linear state. This can result in the formation of clots in the fluid compartment. Such clots might subsequently be expelled into the blood stream. Thus it can be helpful to provide support to the elastic tube by providing a support structure, using a more rigid material, etc. The expansion member 214 can be made of a more rigid material that can be folded accordion style. The internal volume of such a tube can experience less change when its length is altered compared to an elastic tube. However, when its length is shortened, the expansion member 214 can potentially fold over on itself, thus impeding fluid flow through the catheter. The expansion member 214 can thus have a central longitudinal support element therein to provide support and prevent incorrect folding and/or collapse. For example, one or both of the shafts 210, 212 can also serve as supports to the expansion member 214 when the housing 200 moves to the contracted state, allowing the expansion member 214 to fold in an orderly controlled manner, similar to an accordion, rather than collapsing in on itself and potentially blocking the fluid sealed lumen 206 of the housing 200. However, the central longitudinal support element is not limited to one or both of the shafts 210, 212. For example, the central longitudinal support element can include one or more other catheter elements, such as the actuator 700, a wire connected to a temperature sensor (such as a thermocouple) located in a tip of the catheter, a tube containing the actuator and/or thermocouple wire, etc. Because the stretchable tube is prevented from folding over on itself, fluid flow through the catheter in general and the expansion member 214 in particular is not impeded by such folding. In addition, in embodiments where the central longitudinal support element is a tube containing other catheter elements, such as the actuator wire or the wire connected to a thermocouple, these other elements can be isolated from the irrigation fluid and thus any adverse effects on the function of these elements that would result from contact with the irrigation fluid can be minimized. In some embodiments, a portion of the central longitudinal support element itself can include a stretchable element that can serve to reduce or prevent leaks around the actuator wire and/or thermocouple wire. A variety of other supports can be used with the expansion member 214, such as tubes, braces, stiffer materials, pre-formed or folded material that will maintain a more rigid accordion fold when contracted, etc. The fluid sealed lumen 206 can be configured to allow delivery of fluid to the electrode 400 with more consistent flow rates and more ideal fluid pressures, thus helping to provide a smoother function of the device and better irrigation and ablation of tissue.

As indicated above, the proximal end 202 of the housing 200 can be coupled to the elongate body 100, and can be fluidly sealed to prevent any fluid from moving proximally from the fluid sealed lumen 206 of the housing into other proximal parts of the catheter. The proximal end 202 of the housing 200 can be coupled to the elongate body 100 through a variety of means. For example, the elongate body 100 can be heat treated, causing the elongate body 100 to melt around and across an open proximal end of the housing 200, as well as around other components extending therethrough, such as the fluid delivery tube 300 and a sealing shaft 500 that receives the actuator. The process of heating can seal the proximal end 202 of the housing 200, as shown in FIG. 1, forming a cap 800 of melted material and achieving fixation and a fluid seal through one process. A variety of other means for both fixation and sealing can be used, however. For example, the proximal end 202 of the housing 200 can be sealed using a cover, a separate and distinct cap, seal, etc., placed across the opening of the proximal end 202 of the housing 200. An end cap or cover can also be formed as part of the upper tube.

As indicated above, the housing 200 is configured to receive fluid therein and to direct fluid to the electrode. Fluid can be introduced to the housing 200 through a variety of means, such as via a fluid delivery tube 300 extending through an inlet formed in the sealed proximal end of the housing 200. The fluid delivery tube 300 can be configured to deliver fluid through the catheter and into the fluid sealed lumen 206 of the housing 200. The fluid delivery tube 300 can at least partially extend through the catheter and the elongate body 100, for example extending from a proximal end of the catheter and terminating in the fluid sealed lumen 206 of the housing 200. The cap 800 can be formed after the fluid delivery tube 300 is in place, thus sealing the proximal end 202 of the housing 200 and securing the fluid delivery tube 300 in place. However, the fluid delivery tube 300 can be configured to pass through a variety of covers over the proximal end 202 of the housing 200 and can be secured in place through a variety of means, such as by use of adhesive or pins. The fluid delivery tube 300 can be configured to deliver a consistent flow of fluid into the fluid sealed lumen 206.

The electrode 400 can be positioned at a distal end of the elongate body 100, and it can be configured to move between a proximally deployed or vector position, as illustrated in FIG. 1, to an advanced or linear position, as illustrated in FIG. 2. In the retracted position, the electrode 400 can be at least partially retracted into the elongate body 100, and in the expanded position, the electrode 400 can extend distally away from the distal-most end of the elongate body 100. A proximal end of the electrode 400 can be at least partially disposed in the distal end 204 of the expandable and contractible housing 200, expandable along its longitudinal dimension such that it is stretchable. For example, the lower shaft 212 of the housing 200 can attach to the electrode 400 such that a fluid seal can be formed along the engagement of the electrode 400 and the lower shaft 212. This engagement can seal the distal end of the fluid sealed lumen 206 of the housing 200. The electrode 400 can be configured to be moved distally and proximally, which can cause the housing 200 to expand and contract as the lower shaft 212 moves distally and proximally with the electrode 400. The electrode 400 can have one or more fluid paths therethrough configured to allow fluid flow from the fluid sealing lumen 206 to a position distally external from the entire catheter to reach tissue to be irrigated and/or ablated. For example, the electrode 400 can have one or more inlet ports 402 on a proximal half thereof that open inside of the fluid sealed lumen 206 of the housing 200 and connect via one or more fluid channels within the electrode 400 to outlet ports 404 on a distal half thereof that open outside of the catheter entirely. The electrode 400 can thus be configured to receive fluid through the inlet ports 402 from the fluid sealed lumen 206 of the housing 200 and can be configured to expel the fluid from the outlet ports 404 to tissue that is distally positioned in front of the electrode 400. Because the electrode 400 can be sealed to the housing 200 at the distal end of the fluid sealed lumen 206 and because the housing 200 can expand and contract with the electrode 400, irrigation can be performed when the electrode 400 is retracted or advanced (e.g. in either of the deployed or linear states shown in FIGS. 1 and 2).

In order to move the electrode, the end effector 102 can be actuated through a variety of means, such as by use of the actuator 700 illustrated in FIG. 1. The actuator 700 can have a variety of forms, such as one or more wires and/or cables. The actuator 700 can extend through the elongate body 100 between a proximal end of the catheter and the end effector 102. As illustrated in FIG. 1, the actuator 700 can extend through the lumen 206 of the housing 200 and can be fixed to a proximal end of the electrode 400. The actuator 700 can be slidable relative to the elongate body 100 such that the actuator 700 can slide distally and proximally while the elongate body 200 remains unmoved relative to the actuator 700. The actuator 700 can be in the form of a wire that is rigid enough to push the electrode 400 distally into the extended state illustrated in FIG. 2, and strong enough to pull the electrode 400 proximally into the retracted state illustrated in FIG. 1, while still being flexible enough to extend through bending and angled sections of the catheter. The actuator 700 can include an electrically-conductive wire that can deliver energy to the electrode 400 during tissue ablation. The actuator 700 can also have one or more coatings thereon to protect surrounding components from the electrical energy deliverable through the actuator 700 and to protect the actuator 700 from its surrounding environments.

In order to allow the actuator to couple to the electrode, the actuator 700 can be co-axial with the housing 200. The actuator 700 can be configured to extend through the proximal end 202 of the housing 200 and through the fluid sealed lumen 206 to engage with the proximal end of the electrode 400 such that the actuator 700 is slidable relative to the proximal end 202 of the housing 200 while the fluid seal of the fluid sealed lumen 206 is maintained. The fluid seal of the fluid sealed lumen 206 can be maintained even with the slidable actuator 700 disposed therein through a variety of means. For example, a sealing shaft 500 can extend around at least a portion of the actuator 700 and can be configured to create a fluid barrier between the actuator 700 and fluid in the end effector 102, such as the fluid sealed lumen 206. The sealing shaft 500 can extend at least partially through the end effector 102, for example extending from the electrode 400, through the fluid sealed lumen 206 of the housing 200, to the proximal end 202 of the housing 200, and optionally into the proximal part of the catheter. The actuator 700 can extend through a lumen within the sealing shaft 500, and the sealing shaft 500 can thus prevent the fluid in the fluid sealed lumen 206 of the housing 200 from contacting the actuator 700. For example, a distal end of the sealing shaft 700 can be sealably fixed to the proximal end of the electrode 400, and a proximal end of the sealing shaft 500 can extend into and optionally through the proximal end 202 of the housing. The sealing shaft 500 can be fixed in place relative to the proximal end 202 of the housing 200. For example, when the cap 800 is formed, the sealing shaft 500 can be positioned before formation and fixed in place relative to the proximal end 202 of the housing during cap formation. However, the sealing shaft 500 can also be fixed in place through a variety of other means, such as adhesives, pins, engagement with other seals, caps, or covers added to the proximal end 202 of the housing 200, etc.

The sealing shaft 500 can be configured to expand and contract with the housing 200 as the electrode 400 is moved distally and proximally. Because the sealing shaft 500 is able to expand and contract with movement of the electrode 400, the sealing shaft 500 can be configured to provide a sealed passage for the actuator 700 through the fluid sealed lumen 206 of the housing 200, which can protect the actuator 700 and can allow the lumen 206 in the housing 200 to remain fluid sealed even as the actuator 700 is moved back and forth through the proximal end 202 of the housing 200. Without the sealing shaft 500, pressure from the fluid flowing into the housing 200 could cause fluid to flow through the opening in the proximal end 202 of the housing 200 around the actuator 700, and into the rest of the catheter. The required movement of the actuator 700 through the proximal end 202 of the housing 200 makes fluidly sealing the proximal end 202 through other means, such as by use of O-rings, difficult to achieve and consistently maintain. In particular, O-rings or other seals will create friction, thereby preventing movement of the actuator. Accordingly, the sealing shaft 500 allows for free movement of the actuator 700, while fluidly separating the actuator 700 from the fluid sealed lumen 206 of the housing 200, thus allowing fluid to be delivered directly to the electrode.

The sealing shaft 500 can include a flexible sealing portion that is configured to expand and contract with movement of the actuator 700 and the electrode 400. In the illustrated embodiment, a sealing member 502 forms a distal portion of the sealing shaft 500 and is sealed on its distal end to the proximal end of the electrode 400. The proximal end of the sealing member 502 can be sealed to a rigid portion 504 of the sealing shaft 500 that can extend through the proximal end 202 of the housing 200. However, the sealing member 502 can also be sealed directly to the proximal end 202 of the housing 200 and/or a cap, cover, seal, etc. that is used to close the proximal end 202. Alternatively, the sealing member 502 can be integral and unitary with the sealing shaft 500.

When the actuator 700 is moved proximally and distally to move the electrode 400 between the contracted and the expanded states, the sealing member 502 is configured to stretch and contract with movement of the actuator 700 so that the electrode 400 can be moved without breaking the fluid barrier between the fluid sealed lumen 206 of the housing 200, the proximal end 202 of the housing 200, and the actuator 700. The sealing member 502 can be made from any material that can expand and contract, such as various elastomers, plastics, elastics, balloon-like materials, etc. The sealing shaft 500 can also have a rigid portion 504 that extends through the proximal end 202 of the housing 200 and that is configured to be secured in place by the cap 800. The rigid portion 504 can be made of a variety of materials that are configured to withstand the heat treatment applied to the elongate body, such as various plastics or metals.

As indicated above, the catheter also includes at least one expandable member extending between the electrode and the distal end of the elongate body. In an exemplary embodiment, the catheter can include four expandable members positioned equidistant there around. As the electrode 400 advances and retracts, the expandable members 600 that extends between the distal end of the elongate body 100 and the electrode 400 moves between an initial linear configuration for advancement through a body lumen, to flared or expanded configuration. In the deployed configuration, the expandable members can bend around a midpoint there along to extend substantially perpendicular relative to the elongate body 100, as illustrated in FIG. 1, forming a flower pedal shape or propeller blade shape around the electrode 400. The one or more expandable members 600 can be configured to extend longitudinally relative to the elongate body 100 when the electrode 400 is extended distally away from the elongate body 100, as illustrated in FIG. 2. As the electrode 400 and the distal end 204 of the housing 200 extend distally, the expandable members 600 can be configured to flatten against an exterior surface of the housing 200 as the distal end of the catheter takes on a linear shape, as illustrated in FIG. 2. The distal ends of the one or more expandable members 600 can couple to the electrode 400 at a point between the proximal and distal end of the electrode 400, such as at a point corresponding to the engagement between the distal end 204 of the housing 200 and the electrode 400.

The expandable members 600 can each have one or more electrodes disposed thereon and positioned on a distal portion of the expandable member 600 such that each electrode is configured to be approximately perpendicular to the elongate body 100 when the electrode 400 is retracted in the contracted state illustrated in FIG. 1 and each expandable member 600 is in a flared or winged state. The one or more electrodes on the expandable members 600 can be configured to operate in coordination with electrode 400 to provide ablation to a larger surface area of tissue than just the electrode 400 alone. Additional details concerning the catheter generally and the interaction between the expandable member(s) and a central electrode are discussed in detail in U.S. Pat. No. 8,882,761, filed Jul. 15, 2008, U.S. Pat. No.

9,717,558, filed Nov. 7, 2014, and patent application Ser. No. 15/661,606, filed Jul. 27, 2017, all of which are hereby incorporated by reference herein in their entireties. The electrode(s) on the one or more expandable members 600 can be coupled to and receive energy from the actuator 700.

In use, the end effector 102 can be arranged in the linear state as shown in FIG. 2 and the catheter can be advanced through a body lumen of a patient to position the end effector 102 at a surgical site with tissue to be treated, such as tissue requiring ablation and/or irrigation. The actuator 700 can be proximally retracted to proximally retract the electrode 400, causing the end effector 102 to move to the deployed state, as illustrated in FIG. 1, with the expandable members in the expanded configuration. As the electrode 400 is retracted, the housing 200 compresses and reduces in length as the shafts 210, 212 move towards each other and overlap with one another and the expansion member 214 contracts before folding over one or both of the shafts 210, 212 as it compresses entirely. The sealing member 502 of the sealing shaft 500 can also begin compressing and folding together as the actuator 700 retracts the electrode. The catheter can be manipulated to position the electrode 400 and one or more of the expandable members 600 in contact with tissue to be treated. The catheter can be actuated to deliver energy to the electrode 400 and any electrodes arranged on the expandable members 600 and/or to deliver fluid through at least one fluid pathway in the electrode 400. The fluid can flow through the fluid sealed lumen 206 and through the ports 402, 404 in the electrode. When ablation and/or irrigation is finished, the actuator 700 can be pushed distally to cause the end effector 102 to return to the linear state. The housing 200 can expand in length as the shafts 210, 212 move away from each other and the expansion member 214 expands to keep the shafts 210, 212 engaged with each other while allowing the shafts 210, 212 to move away. The sealing member 502 of the sealing shaft 500 also can unfold and expand as the electrode 400 moves distally. The catheter can be maneuvered to another site or removed from the patient. Because of the expandable and contractible fluid channel in the end effector 102, fluid can be successfully delivered to tissue with the end effector 102 in the expanded state, allowing ablation with fluid and/or irrigation to be performed successfully in the expanded state. The catheter(s) disclosed herein can be steered through a variety of means, which are well-known in the art.

Figure 3:
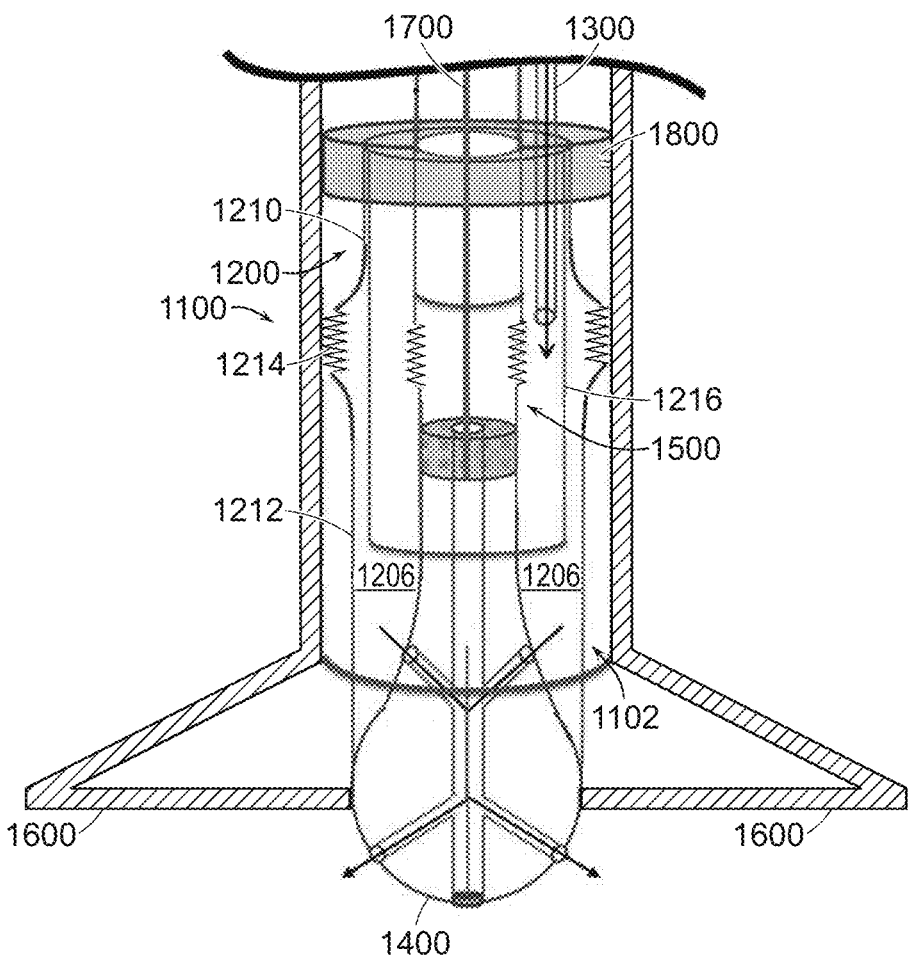
FIG. 3 is a cross-sectional, partially-perspective side view of another embodiment of a distal end of a catheter with an end effector in a deployed, expanded state.

Catheters with expandable and contractible fluid pathways extending therethrough can have a variety of other configurations. For example, FIG. 3 illustrates a catheter with an expandable and contractible fluid pathway similar to the catheter of FIGS. 1 and 2. FIG. 3 illustrates a distal end of a catheter with an elongate body 1000. The elongate body 1000 can have a proximal end, a distal end, and a lumen extending at least partially therethrough. An end effector 1102 is disposed at least partially within the distal end of the elongate body 1100, similar to the end effector 102 of FIGS. 1 and 2. The end effector 1102 can include an expandable and contractible housing 1200 having a fluid delivery tube 1300 and an electrode 1400 at a distal end thereof and defining a fluid outlet. An expandable and contractible sealing shaft 1500 can extend within the housing 1200 from a proximal end to the distal end. The device can also include at least one expandable member or wing 1600 extending between the distal end of the elongate body 1100 and the electrode 1400. An actuator 1700 can also extend through the device and it can be configured to actuate the end effector 1102. Upon actuation of the actuator 1700, the electrode 1400 can be configured to distally advance and proximally retract relative to the elongate body 1100, which can cause the expansion and the contraction of various components within the elongate body.

The expandable and contractible housing 1200 can be similar to the housing 200, having a fluid sealed lumen 1206 therethrough. The housing 1200 can include an upper shaft 1210, a lower shaft 1212, and an expansion member 1214. A proximal end of the expansion member 1214 can be attached to a distal end of the upper shaft 1210, and a distal end of the expansion member 1214 can be attached to a proximal end of the lower shaft 1212. The upper shaft 1210 can be sealably fixed at a proximal end to the elongate body 1100, such as at a melted cap 1800, and the lower shaft 1212 can be sealably fixed to the electrode 1400. The upper and lower shafts 1210, 1212 can be configured to move towards and away from each other upon movement of the electrode 1400. However, the shafts 1210, 1212 can be configured not to overlap each other. Instead, the expansion member 1214 can extend therebetween, and a support shaft 1216 can have a proximal end fixed to a proximal point in the elongate body 1100, similar to the upper shaft 1210, and the support shaft 1216 can extend distally within the housing 1200 to provide support to the expansion member 1214 (instead of support being provided by the upper and/or lower shafts 210, 212 as provided in FIGS. 1 and 2). The support shaft 1216 can terminate at a point distal of the expansion member 1214 when the expansion member 1214 is in its contracted state so that the expansion member 1214 can fold in an orderly, controlled way, like an accordion, as it contracts rather than collapsing in on itself and potentially blocking the fluid sealed lumen 1206 of the housing 1200.

Figure 4:
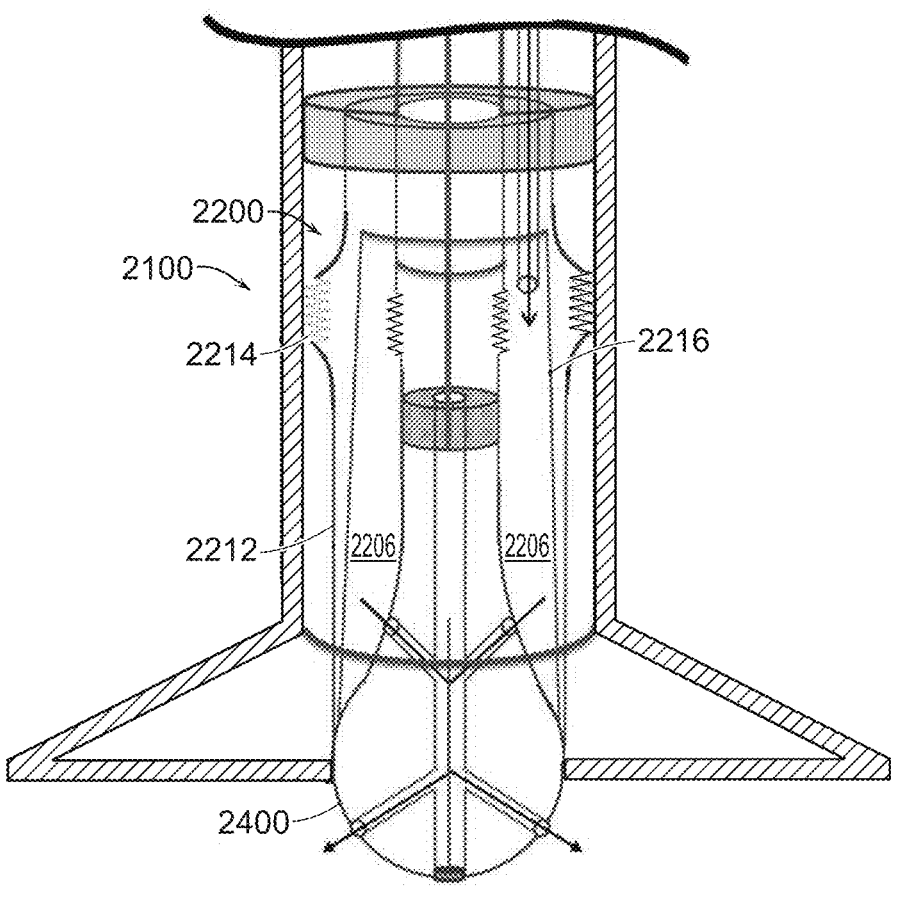
FIG. 4 is a cross-sectional, partially-perspective side view of another embodiment of a distal end of a catheter with an end effector in a deployed, expanded state.

While the support shaft 1216 is fixed in a proximal position in FIG. 3, the support shaft can be attached at various positions. For example, FIG. 4 illustrates a catheter with an elongate body 2100 and an expandable and contractible fluid pathway similar to the catheters of FIGS. 1 and 3. In this embodiment, the support shaft 2216 can have a distal end fixed to a proximal portion of the electrode 2400, similar to the lower shaft 2212, and the support shaft 2216 can extend proximally within the housing 2200 to provide support to the expansion member 2214. The support shaft 2216 can terminate at a point proximal of the expansion member 2214 when the expansion member 2214 is in its contracted state so that the expansion member 2214 can fold in an orderly, controlled way, like an accordion, as it contracts rather than collapsing in on itself and potentially blocking the fluid sealed lumen 2206 of the housing 2200.

Figure 5:
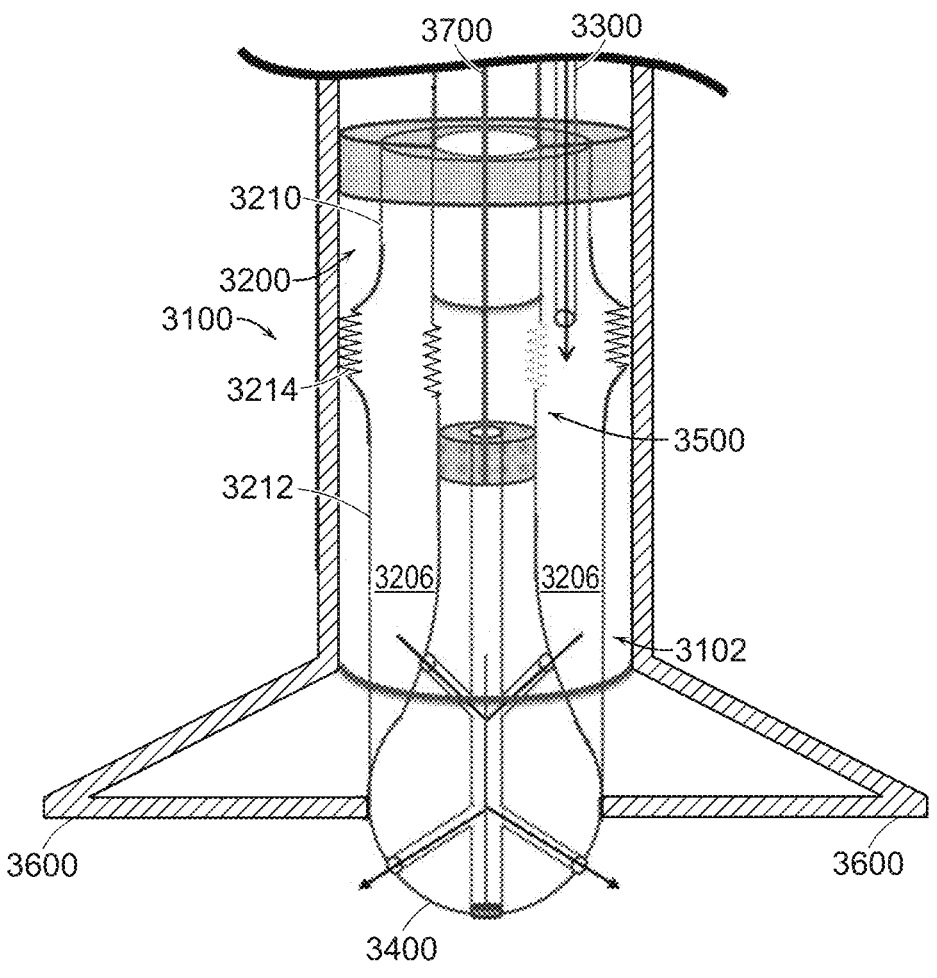
FIG. 5 is a cross-sectional, partially-perspective side view of another embodiment of a distal end of a catheter with an end effector in a deployed, expanded state.

The expansion member can also be configured such that no support structure is required. For example, FIG. 5 illustrates a catheter with an expandable and contractible fluid pathway similar to the catheters of FIGS. 1-4. FIG. 5 illustrates a distal end of a catheter with an elongate body 3100. The elongate body 3100 can have a proximal end, a distal end, and a lumen extending at least partially therethrough. An end effector 3102 is disposed at least partially within the distal end of the elongate body 3100, similar to the end effector 102 of FIGS. 1 and 2. The end effector 3102 can include an expandable and contractible housing 3200, a fluid delivery tube 3300, and an electrode 3400 at a distal end thereof. An expandable and contractible sealing shaft 3500 can extend within the housing 3200 from a proximal end to the distal end. The catheter can also include at least one expandable member or wing 3600 extending between the distal end of the elongate body 3100 and the electrode 3400, and an actuator 3700 extending through the elongate body and configured to actuate the end effector 3102. Upon actuation of the actuator 3700, the electrode 3400 can be configured to distally advance and proximally retract relative to the elongate body 3100, which can cause the expansion and the contraction of various components within the elongate body.

The expandable and contractible housing 3200 can be similar to the housing 200, having a fluid sealed lumen 3206 therethrough. The housing 3200 can include an upper shaft 3210, a lower shaft 3212, and an expansion member 3214. However, the expansion member 3214 can be configured to be rigid enough not to collapse in on itself while still being able to contract and expand. For example, the expansion member 3214 can be formed of semi-rigid panels that are configured to fold in an accordion style as they contract and extend linearly as they expand.

Figure 6:
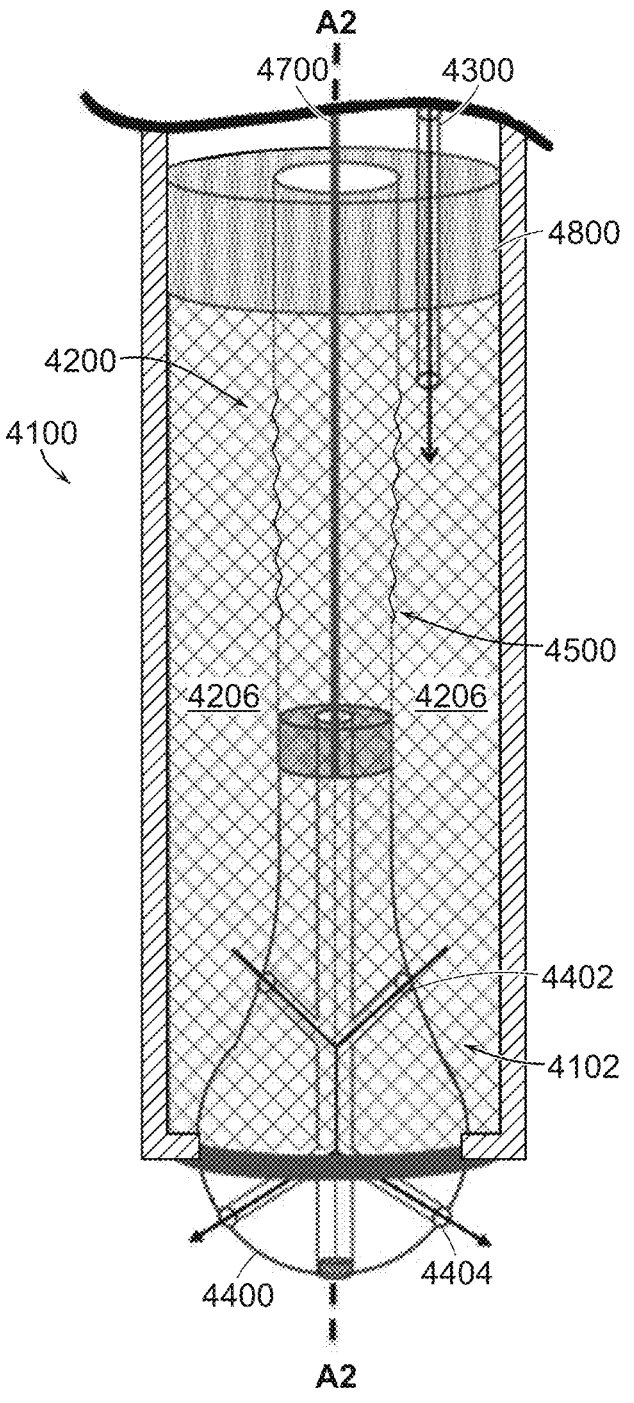
FIG. 6 is a cross-sectional, partially-perspective side view of another embodiment of a distal end of a catheter with an end effector in a collapsed, linear state.
Figure 7:
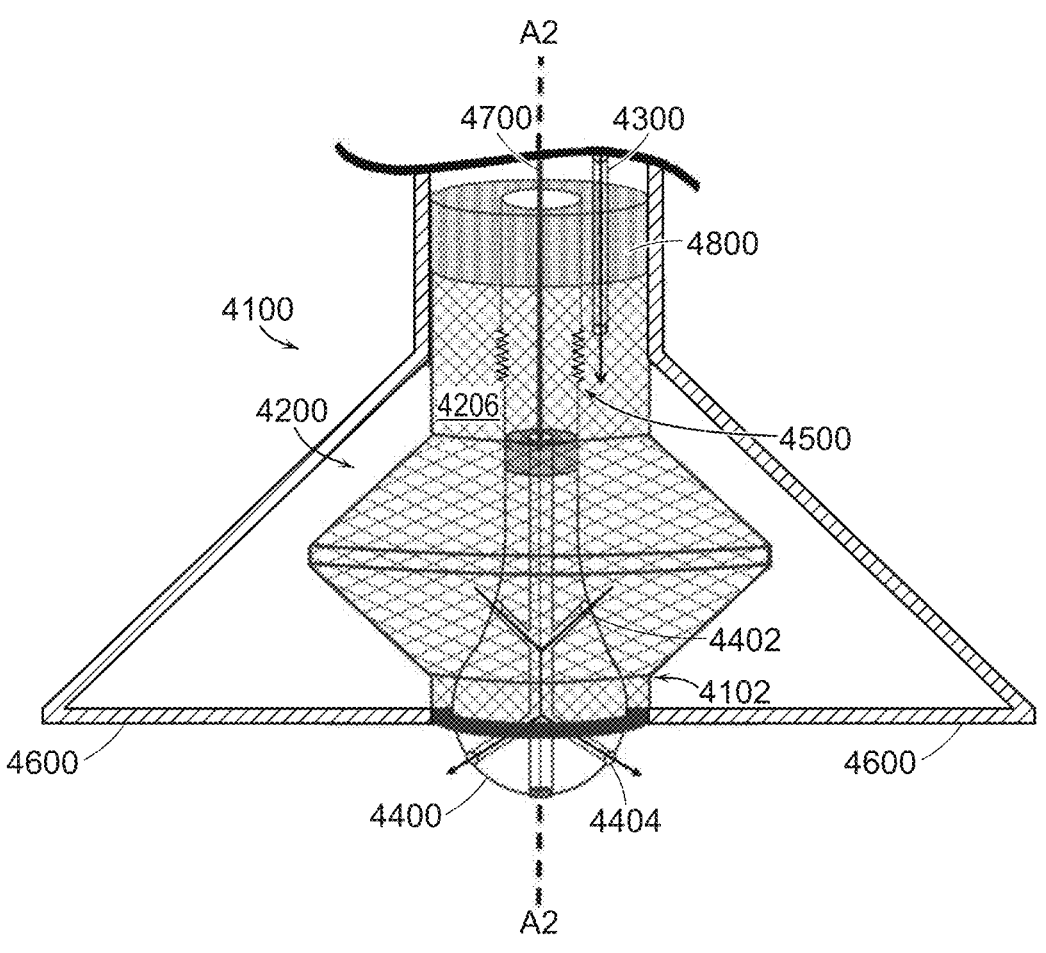
FIG. 7 is a cross-sectional side view of the distal end of the catheter of FIG. 6 with the end effector in a deployed, expanded state.

The expandable and contractible housing can also be configured in the form of a flexible tube. For example, FIGS. 6 and 7 illustrate a catheter with an expandable and contractible fluid pathway similar to the catheters of FIGS. 1-4. FIGS. 6 and 7 illustrate a distal end of a catheter with an elongate body 4100. The elongate body 4100 can have a proximal end, a distal end, and a lumen extending at least partially therethrough. An end effector 4102 is disposed at least partially within the distal end of the elongate body 4100, similar to the end effector 102 of FIGS. 1 and 2. The end effector 4102 can include an expandable and contractible housing 4200, a fluid delivery tube 4300, and an electrode 4400 at a distal end thereof. An expandable and contractible sealing shaft 4500 can extend within the housing 4200 from a proximal end to the distal end. The catheter can also include at least one expandable member or wing 4600 extending between the distal end of the elongate body 4100 and the electrode 4400, which in various embodiments can have one or more peripheral electrodes thereon. An actuator 4700 can extend through the elongate body and it can be configured to actuate the end effector 4102. Upon actuation of the actuator 4700, the electrode 4400 can be configured to distally advance and proximally retract relative to the elongate body 4100, which can cause the expansion and the contraction of various components within the elongate body. For example, distal movement of the actuator 4700 can cause distal advancement of the electrode 4400, which can cause the expandable member or wing(s) 4600 to collapse or compress into a linear configuration, as shown in FIG. 6, and proximal movement of the actuator 4700 can cause the electrode 4400 to retract proximally, thereby causing the expandable member or wing(s) 4600 to expand, as shown in FIG. 7.

The expandable and contractible housing 4200 can be similar to housing 200, creating a fluid sealed lumen 4206 therethrough. However, the expandable and contractible housing 4200 in this embodiment is in the form of a flexible tube that expands radially outward in a direction perpendicular to a longitudinal axis A2 of the housing 4200 as the housing 4200 is compressed in a direction parallel to the axis A2. In some embodiments, when the actuator 4700 is actuated to pull the electrode 4400 proximally and to move the at least one wing 4600 to an expanded configuration (such as illustrated in FIG. 7), the housing 4200 can be configured such that it remains within a space within the at least one expanded wing 4600. A proximal end of the housing 4200 can be sealably fixed to a proximal end of the elongate body 4100, such as at a melted cap 4800, and a distal end of the housing 4200 can be sealably fixed to the electrode 4400 at a location distal to fluid inlet ports 4402 and proximal to fluid outlet ports 4404 in the electrode 4400. The housing 4200 can be sealably fixed circumferentially around the electrode 4400 so that fluid cannot leak from the lumen 4206 inside the housing 4200 to any space outside the housing 4200.

In various embodiments, the expandable and contractible housing 4200 can be in the form of a flexible tube with a smooth surface both in a collapsed, linear configuration, as shown in FIG. 6, and in an expanded, deployed configuration, as shown in FIG. 7. The smooth surface of the flexible tube can have a low likelihood of trapping any material, such as blood or tissue, as trapped blood or tissue material can potentially clot and form small emboli that would pose a risk to the patient. The housing 4200 can be made of a variety of materials. For example, the housing can be formed from a flexible braid, such as flexible metal braids, and in some embodiments, the metal braid can be coated with a flexible sealing material so that fluid does not pass through a wall of the housing. The flexible braids can be made of a variety of materials. For example, the metal braid can be constructed from steel strands and/or nitinol strands. In some embodiments, nitinol strands can be used to allow the housing to revert to a pre-determined shape when external forces are not acting upon it. For example, the housing can be biased to the collapsed, linear configuration. The flexible sealing material can include a variety of materials, such as a plastic and/or rubber material (like silicone) that is deposited on the metal braid. The combination of metal braids and flexible sealing materials can allow the housing to withstand a pressure of fluid contained within the lumen 4206 of the housing 4200 while the housing 4200 remains flexible, allowing the housing 4200 to be rigid enough not to collapse in on itself while still being able to contract and expand. Thus, in some embodiments, the housing 4200 can define the lumen 4206. In some embodiments, the proximal portion of the housing 4200 is covered by a rigid plastic sleeve in order to constrain the proximal portion of the housing to maintain a cylindrical shape as shown in FIG. 7. Furthermore, the coated metal braid can cover a portion of the electrode 4400 not in direct contact with tissue, for example covering at least some or all of the electrode 4400 not in direct contact with tissue, and thereby can serve as a Faraday cage, blocking energy from spreading to blood and tissue not in direct contact with the electrode 4400. Such a spread of energy to non-targeted regions can potentially be undesirable from efficacy, efficiency, and patient safety perspectives. Thus, the majority or all of the energy can be directed instead through the electrode 4400 and into tissue.

In some embodiments, the housing 4200 can be configured so that a volume of fluid inside the lumen 4206 experiences little to no change when the housing 4200 moves between its collapsed and expanded configurations. For example, the volume of the lumen 4206 can change less than about 50 percent, and more preferably less than about 25 percent, and even more preferably less than about 10 percent. The volume remaining substantially unchanged can be caused by, for example, the braided and coated construction of the housing 4200, which permits the housing 4200 to change drastically in shape (such as moving from the collapsed configuration to the expanded configuration) while minimizing loss in internal volume. Allowing minimal change to the volume of the lumen 4206 can help to minimize an amount of fluid entering and/or being expelled from the lumen 4206 when the housing 4200 is moved between the collapsed and expanded configurations. Minimizing the amount of fluid entering and/or being expelled from the lumen 4206 when the housing 4200 moves between its collapsed and expanded configurations can be helpful because such changes in volume might involve blood entering and being expelled from the housing 4200, and such blood might potentially clot and form emboli that can pose a risk to a patient.

In various embodiments, the expandable and contractible housing can be configured and constructed of material that will spontaneously revert to a pre-specified form when external forces are not acting upon it, such as nitinol as mentioned above. For example, the housing 4200 can be constructed to revert to an elongated cylindrical form when an external force is not compressing it along the direction parallel to the axis A2 of the housing 4200. In such an embodiment, when the actuator 4700 is released from retracting the electrode 4400 proximally, the housing 4200 will elongate and consequently the elongate body 4100 will revert to the collapsed, linear configuration, shown in FIG. 6. By causing the housing 4200 to revert to an elongated cylindrical form, any wire used for the actuator 4700 does not need to be as stiff because a user, after using the electrode 4400 in the expanded configuration, would not need to be able to push the electrode 4400 distally into the collapsed configuration. If the user were required to push the actuator 4700 distally to cause the electrode 4400 to move distally, the wire would need to be made from a thick, relatively stiff material. A thicker wire can take up more space inside the catheter, which in turn may require a catheter having a larger diameter. This is undesirable as such a catheter can potentially be more difficult to maneuver through narrow blood vessels, and a larger catheter could potentially create a larger opening if the catheter were intentionally pushed through normally closed biological structure, such as the foramen ovale. Additionally, a stiffer wire can potentially make the entire catheter stiffer and less flexible, which may make it more difficult to maneuver the catheter inside a body of a patient. In various embodiments, the housing can be the flexible tube itself, and in other embodiments, the housing can surround the flexible tube such that the flexible tube as described above is within the housing.

A person skilled in the art will appreciate that, while not shown, any handle assembly known in the art can be used in combination with the catheter assemblies disclosed herein. The handle assembly can include any number of features, such as steering mechanisms for steering the catheter, actuation knobs, levers, buttons or the like for controlling the actuator, and for controlling fluid and energy delivery.

In the present disclosure, like-numbered components of the embodiments generally have similar features, and thus within a particular embodiment each feature of each like-numbered component is not necessarily fully elaborated upon. Sizes and shapes of the devices described herein, and the components thereof, can depend at least on the anatomy of the subject in which the devices will be used, the size and shape of components (e.g., spinal rods) with which the devices will be used, and the methods and procedures in which the devices will be used. The figures provided herein are not necessarily to scale. Although the devices and methods disclosed herein are generally directed to surgical techniques, they can also be used in applications outside of the surgical field. Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A method for treating tissue, comprising:

advancing a catheter to position at least one electrode to be in direct contact with tissue to be treated, the catheter including a plurality of expandable wings, the at least one electrode having a portion covered by a Faraday cage and being located at the distal end of the catheter;

translating the at least one electrode in a longitudinal direction to radially expand the plurality of expandible wings and to longitudinally compress the Faraday cage; and delivering energy to the at least one electrode to ablate the contacted tissue to be treated, wherein the Faraday cage blocks energy from passing from the portion of the at least one electrode covered by the Faraday cage to surrounding blood and tissue not in direct contact with the at least one electrode.

2. The method of claim 1, wherein the Faraday cage comprises a metal braid.

3. The method of claim 2, wherein a sealing material covering the metal braid prevents fluid from passing through the metal braid.

4. The method of claim 3, wherein the sealing material is flexible.

5. The method of claim 2, wherein the metal braid is flexible.

6. The method of claim 1, wherein the energy delivered is electrical energy.

7. The method of claim 1, wherein the energy delivered is radiofrequency energy.

8. The method of claim 1, further comprising delivering fluid to the electrode while energy is being delivered.

9. A method for treating tissue, comprising:

advancing a catheter to position at least one electrode to be in direct contact with tissue to be treated, the at least one electrode having a portion covered by a longitudinally-compressible Faraday cage and being located at a distal-most end of the catheter; and delivering energy to the at least one electrode to ablate the contacted tissue to be treated, wherein the Faraday cage blocks energy from passing from the portion of the at least one electrode covered by the Faraday cage to surrounding blood and tissue not in direct contact with the at least one electrode.

10. The method of claim 9, wherein the Faraday cage comprises a metal braid.

11. The method of claim 9, wherein the energy delivered is electrical energy.

12. The method of claim 9, wherein the energy delivered is radiofrequency energy.

13. A method for treating tissue, comprising:

advancing at least one electrode to directly contact tissue to be treated, the at least one electrode at least partially surrounded by a longitudinally-compressible Faraday cage; and delivering energy to the at least one electrode to ablate the directly-contacted tissue to be treated, the delivered energy being blocked by the Faraday cage from passing from the at least one electrode to blood and tissue surrounding the directly-contacted tissue.

14. The method of claim 13, wherein the Faraday cage comprises a metal braid.

15. The method of claim 14 wherein the metal braid is coated with a sealing material.

16. The method of claim 13, wherein the energy delivered is electrical energy.

17. The method of claim 13, wherein the energy delivered is radiofrequency energy.

* * * * *